United States Patent [19]

Rule

[11] Patent Number: 4,792,634
[45] Date of Patent: Dec. 20, 1988

[54] PROCESS FOR THE PREPARATION OF ARYL SULFIDES

[75] Inventor: Mark Rule, Kingsport, Tenn.

[73] Assignee: Eastman Kodak Company, Rochester, N.Y.

[21] Appl. No.: 87,332

[22] Filed: Aug. 20, 1987

[51] Int. Cl.$^4$ .............................................. C07C 148/00
[52] U.S. Cl. ..................................... 568/58; 546/153; 546/157; 546/178; 546/261; 549/51; 549/52; 549/59; 549/466; 549/472; 564/430; 568/29; 568/42; 568/49; 568/57
[58] Field of Search ............... 568/29, 53, 57, 58, 568/42, 49, 25; 564/430; 546/261, 157, 153, 178; 549/472, 466, 59, 51, 52

[56] References Cited

U.S. PATENT DOCUMENTS

| | | | |
|---|---|---|---|
| 2,538,941 | 1/1951 | Macallum | 568/38 |
| 2,903,484 | 9/1959 | Hardy et al. | 568/58 |
| 3,322,834 | 5/1967 | Hill et al. | 568/58 |
| 3,397,244 | 8/1968 | Louthan | 568/58 |
| 3,706,805 | 12/1972 | Fujisawa et al. | 568/58 |
| 4,010,210 | 3/1977 | Voronkov et al. | 568/58 |
| 4,035,424 | 7/1977 | Deryagina et al. | 568/58 |
| 4,044,056 | 8/1977 | Hawkins | 568/58 |

OTHER PUBLICATIONS

Inorg. Macromol. Rev., vol. 1, (1970), pp. 101–113, M. Schmidt.
Comprehensive Inorganic Chemistry, vol. 2, J. C. Bailar et al, 1973.
E. Reid, Organic Chemistry of Bivalent Sulfur, vol. II, pp. 21–23 (1960), Chem. Publishing, Co. Inc., N.Y.

*Primary Examiner*—Mary E. Ceperley
*Attorney, Agent, or Firm*—Charles R. Martin; William P. Heath, Jr.

[57] ABSTRACT

A method for preparing aryl sulfides by heating an iodoaromatic compound with elemental sulfur at a temperature above about 150° C.

11 Claims, No Drawings

PROCESS FOR THE PREPARATION OF ARYL SULFIDES

BACKGROUND OF THE INVENTION

1. Field of the Invention

The invention relates to a process for the preparation of aryl sulfides by heating an iodoaromatic compound in the presence of elemental sulfur.

2. Discussion of the Background

Aryl sulfides are useful as industrial chemicals, such as mothproofing agents, herbicides, lubricants, antioxidants, organic semiconductors, plasticizers, high boiling point solvents, etc. Additionally, they are useful as intermediates for the preparation of insecticides and pharmaceuticals. Aryl sulfides generally have a wide fluid range having a low melting point and a relatively high boiling point. This behavior makes these compounds particularly suitable for use as heat transfer media and as mineral oil additives. A relatively simple, economic process for the preparation of these aryl sulfides is therefore of continued economic and industrial significance.

Several methods for preparing aryl sulfides are known. Typically, aryl sulfides such as phenyl sulfide have been prepared by the reaction of aryl halides with metal sulfides in polar solvents, often with copper salts as catalysts. U.S. Pat. Nos. 3,322,834 and 3,397,244 disclose methods of preparing aryl sulfides by heating aryl halides with an alkali metal sulfide and an alkali metal bisulfide, respectively. Alternatively, aryl sulfides can be prepared by reacting aromatic compounds with a sulfur chloride (U.S. Pat. No. 3,706,805) or by reacting a chloro- or bromo-aromatic compound with hydrogen sulfide at elevated temperatures (U.S. Pat. No. 4,010,210). A method is also known in which a naphthol and hydrogen sulfide are reacted to produce thionaphthols and naphthyl sulfides (U.S. Pat. No. 2,903,484). Aryl sulfides have also been produced by a disproportionation reaction by heating unsymmetrical aromatic sulfides at elevated temperatures (U.S. Pat. No. 4,044,056) and by heating aromatic thiols at high temperatures in the presence of an inert gas (U.S. Pat. No. 4,035,424).

A relatively simple procedure for preparing aryl sulfides is to heat an aryl chloride in the presence of elemental sulfur. The reaction of aryl chlorides with sulfur is disclosed by M. Schmidt (Inorg. Macromol. Rev. 1 (1970) 101). However, this reaction yields a complex mixture of products, which are mostly polymeric.

A need exists, therefore, for a simple industrial process for preparing aryl sulfides which is economical, efficient, and which produces high yields. Additionally, a simple high yield process which does not involve tedious workup procedures is preferred.

SUMMARY OF THE INVENTION

Accordingly, one object of the present invention is to provide a simple high yield process for the preparation of aryl sulfides.

Another object of the invention is to provide a method for the preparation of aryl sulfides which avoids tedious workup procedures and which produces little or no polymeric side products.

These and other objects of the present invention which will become apparent from the following specification have been achieved by the present method for preparing aryl sulfides which comprises reacting a mixture of an iodoaromatic compound with elemental sulfur at a temperature above about 150° C.

DETAILED DESCRIPTION OF THE PREFERRED EMBODIMENTS

The process of the present invention involves reacting an iodoaromatic compound in the presence of elemental sulfur at a temperature above about 150° C. The reaction evolves elemental iodine and produces aryl sulfides in high yield which may be isolated by conventional means.

By "iodoaromatic compound" is meant a compound having an aromatic ring structure with a single iodine substituent. Additional substituents, other than iodine, may be present however. Iodoaromatic compounds which are suitable for use in the present process include hydrocarbon aromatics, nitrogen-containing aromatics, sulfur-containing aromatics and oxygen-containing aromatics. Typical hydrocarbon aromatics include benzene and condensed ring aromatics such as naphthalene and anthracene. Typical sulfur-containing aromatics are, for example, thiophene and benzothiophene. Typical nitrogen-containing aromatics include aniline, pyridine and quinoline, for example. Typical oxygen-containing aromatics include furan, benzofuran, etc. Additionally, substituted aromatics are suitable for use in the present invention including aromatic sulfones, diaryl ethers, diaryl carbonyls, diaryl sulfides and the like.

The aromatic starting materials may be unsubstituted or substituted by at least one alkyl group having from 1-6 carbon atoms. Especially preferred alkyl groups are methyl, ethyl, propyl, and butyl groups.

Additional substituents which may also be present on the aromatic compounds are essentially unlimited. These substituents may include, for example, phenyl, halogen, such as fluoro, chloro, and bromo, as well as hydroxy, nitro, amino, alkoxy, and carboxylate and carboxylic acid substituents, as well as aryl sulfones and aryl ketones.

The spatial arrangement of these substituents on the aromatic starting material is not critical and the substituent may be present on a carbon atom adjacent to the carbon atom bearing the iodine or may be present on a carbon atom further removed from the iodine bearing carbon. The spatial arrangement of these substituents is preserved in the present reaction.

Preferred iodoaromatic compounds include unsubstituted or substituted hydrocarbon aromatics which have a single iodine substituent. Specific examples include substituted and unsubstituted iodobenzenes, iodonaphthalenes, iodobiphenyls, and higher aromatic compounds having a single iodine substituent such as iodoanthracene or iodophenanthrene. These aromatics may be substituted with one or more alkyl groups having from 1-6 carbon atoms. The alkyl substituents may be straight chain, branched or cyclic.

Particularly preferred iodoaromatic compounds are iodobenzene, iodonaphthalene, iodobiphenyl and alkyl derivatives thereof. Especially preferred iodoaromatic compounds are iodobenzene, 1- and 2-iodonaphthalene, iodobiphenyls and iodotoluenes.

The iodoaromatic starting materials of the present invention may be prepared by any suitable process. For example, the iodoaromatic compounds may be prepared by standard liquid phase process such as those disclosed in U.S. Pat. No. 4,240,987 and Russian Pat. No. 159,496 as well as by other conventional iodination reactions such as those disclosed in U.S. Pat. Nos. 3,363,010; 2,998,459; EP183,579; 181,790; 171,256; Japan Pat. Nos. 82/77631; and 85/224644. Although the iodoaromatic compounds may be prepared by any such process, the preferred method of preparing the iodoaromatic compounds is that disclosed in copending application Ser. Nos. 912,806, filed Sept. 9, 1986, now U.S. Pat. No. 4,746,758; 029,896, filed Mar. 25, 1987; 029,959, filed Mar. 25, 1987; 029,897, filed Mar. 25, 1987 and 029,898, filed Mar. 25, 1987. Alternatively, the iodoaromatic starting materials may be produced by a transiodination process such as that disclosed in copending application Ser. Nos. 029,899, filed Mar. 25, 1987; 029,956, filed Mar. 25, 1987 and 029,949, filed Mar. 25, 1987. The disclosures of these copending applications are incorporated herein by reference for a more complete description of these preferred processes for preparing the iodoaromatic starting materials.

Sulfur is reacted as elemental sulfur and may consist of any of the standard forms which are possible for elemental sulfur. That is, the sulfur may be present in any of its allotropic modifications such as orthorhombic, cyclooctasulfur ($S_8$) or any other cyclic elemental sulfur such as any of the cyclosulfur species having 6-12 sulfur atoms. Additionally, any crystalline form of sulfur may be used in the present reaction. Surprisingly, the presence of impurities in the sulfur does not affect the progress or high yield of the reaction. This is advantageous, since crude sulfur containing impurities such as, for example iron, may be used without detrimental effect in the reaction. The sulfur preferably has a purity of about 95%-100%, although sulfur having a higher degree of impurity may also be used.

The reaction may be carried out neat (without solvent) by merely heating and reacting the sulfur and iodoaromatic compound. Under these conditions, the iodoaromatic compound itself acts as a solvent for the sulphur producing a reaction melt and enabling a facile and complete reaction. Alternatively, the iodoaromatic compound can be dissolved in an organic solvent which is inert to the reaction conditions, i.e., does not react with iodine or sulfur. Examples of suitable solvents include aromatic hydrocarbons such as benzene, naphthalene, toluene, xylene, etc. as well as diaryl sulfides, diaryl ethers and diaryl sulfones. It is preferable to conduct a reaction in a solvent which is related to the iodoaromatic compound being reacted. For example, when reacting iodobenzene in the presence of sulfur, it is preferable to use benzene or toluene as the solvent.

The iodoaromatic compound and sulfur are preferably heated at a temperature above about 150° C. Although the reaction may be conducted at temperatures below 150° C., the reaction is much slower at lower temperatures and side products such as diaryl disulfides are observed. When the reaction is conducted at temperatures below about 150° C., the disulfides produced may be isolated from the reaction melt and provide a source of diaryl disulfides for other reaction processes. Alternatively, additional iodoaromatic compound may be added to the reaction melt to react with the diaryl disulfides producing additional aryl sulfide products.

The reaction is preferably conducted at temperatures above 180° C. to ensure reasonable reaction times and limit undesired side products. The upper temperature limit is essentially the temperature at which the iodoaromatic compound begins to thermally decompose. Temperatures in the range of 150°-400° C. are generally sufficient for most iodoaromatic starting materials. However, reaction temperatures in excess of 400° C. are considered to be within the scope of the present invention. Preferred reaction temperatures are from about 180°-350° C.

Reaction times range from approximately ½ hour to about 10 hours. Theoretically, there is no limit to the length of the reaction time since the aryl sulfides produced are thermally stable; however, reaction times in the range of ½ to 5 hours have been found to be sufficient to achieve relatively high yields. The optimum reaction times and temperatures are dependent on the specific iodoaromatic compounds used and can be readily determined by those skilled in the art.

At temperatures above about 150° C., sulfur reacts with the iodoaromatic compound evolving elemental iodine and forming the aryl sulfide according to the reaction shown below:

The reaction can be performed with a slight excess of sulfur or aromatic iodide present in the reaction mixture. When excess sulfur is used, small amounts of aryl disulfides and polysulfides are formed. Preferably, therefore, a stoichiometric amount of sulfur should be utilized. In this way, the reaction products are essentially entirely the aryl sulfide and elemental iodine.

Elemental iodine is evolved from the reaction melt or solution during the course of the reaction. Removal of the evolved iodine insures that the reaction will go to completion. The iodine may be removed by any suitable process such as, for example, bubbling air or an inert gas such as nitrogen or argon through the reaction melt or solution, or by applying a vacuum to the reaction vessel.

The progress of the reaction can be monitored by quantitatively evaluating the iodine evolved. This can be performed by collecting and weighing the iodine or by weighing the product aryl sulfide and determining the amount of iodine evolved by a standard weight-loss method. Alternatively, standard gas chromatography (GC) or combined gas chromatography-mass spectrometry (GC-MS) techniques may be used to evaluate progress of the reaction.

Once formed, the product aryl sulfides can be isolated from the reaction mix or solution by standard techniques such as crystallization or distillation.

The iodine which is evolved can likewise be collected and is directly suitable as a commercial product or as a feedstock for other chemical processes.

It is not necessary to stir or agitate the reaction melt or solution, although stirring and agitation generally increase the efficiency of the reaction. When agitation is desired, mechanical stirring may be effected or the agitation may be provided by means of bubbling an inert gas or air through the reaction melt or mixture. The latter agitation method is preferred since the iodine which is evolved may be simultaneously carried from the reaction melt or solution by the gas flow. Typically, a continuous reaction vessel will be charged with the starting materials and an inert gas such as nitrogen will be passed in a counterflow direction relative to the material flow in the reactor. The passage of nitrgen through the continuous reactor agitates the reaction melt and at the same time sweeps the iodine evolved in the reaction from the continuous reactor.

When run as a batch process, the air or inert gas is simply bubbled through the reaction vessel which may optionally be mechanically stirred.

It is surprising that the present reaction which utilizes iodoaromatic compounds and sulfur produces primarily the aryl sulfides whereas the corresponding reaction with aryl chlorides produces a complex mixture of products which are largely polymeric in nature. The high yields and lack of side products in the present reaction make it uniquely suited for industrial and commercial applications. Product conversions of 50 to 100 percent can readily be obtained, with the only significant reaction byproducts being the corresponding diaryl disulfides and unreacted aryl iodides. Since these byproducts can be recycled to yield diaryl sulfides, the yield of the reaction can be made essentially quantitative.

Other features of the invention will become apparent in the course of the following descriptions of exemplary embodiments which are given for illustration of the invention and are not intended to be limiting thereof.

EXAMPLES

In the following examples, the reactionbetween an iodoaromatic compound and sulfur was carried out in a reaction tube which was heated for the times indicated in each example (see Table 1). The anaysis of the products was carried out by GC and by GC-MS.

EXAMPLE 1

After heating for 30 minutes, and iodine color was noted in the reaction solution. After 24 hours, the reaction was stopped. The reaction mixture contained iodobenzene, diphenyl sulfide, and small amounts of diphenyl disulfide. Conversion of the iodobenzene was 55%.

EXAMPLE 2

After 5 minutes, copious fumes of iodine revolved from the reaction mixture. After about 3 hours, iodine evolution essentially ceased. GC-MS of the reaction product found mainly bis(1-naphthalene)sulfide. Conversion of the 1-iodonaphthalene was 95%.

EXAMPLE 3

The reaction mixture was allowed to react for 3 hours. GC-MS of the reaction product found bis(4-biphenyl)sulfide, with only traces of the disulfide as a reaction coproduct. Conversion of the iodobiphenyl was 97%.

EXAMPLE 4

After 3 hours, the reaction mixture showed a mixture of di(p-tolyl)sulfide and di(p-tolyl)disulfide by GC-MS. No isomeric ditolyl sulfides or disulfides were found. Conversion of the 4-iodotoluene was 73%.

COMPARATIVE EXAMPLE 5

Heating 4-iodobiphenyl for 10 hours at 230° C. caused little discoloration of the solution and no iodine evolution. Thus, the iodoaromatic is thermally stable under the reaction conditions in the absence of sulfur.

TABLE 1

| Example | Iodoaromatic Compound (g) | Sulfur (g) | Temp. |
| --- | --- | --- | --- |
| 1 | Iodobenzene (2.04) | 0.32 | 180° C. |
| 2 | 1-iodonaphthalene (2.54) | 0.32 | 230° C. |
| 3 | 4-iodobiphenyl (2.80) | 0.32 | 230° C. |
| 4 | 4-iodotoluene (2.18) | 0.32 | 210° C. |
| 5 | 4-iodobiphenyl (2.80) | — | 230° C. |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for preparing aromatic sulfides, consisting essentially of: reacting a mixture of an iodoaromatic compound, said compound having a single iodine ring substituent and elemental sulfur at a temperature above about 150° C.

2. The method of claim 1, wherein said iodoaromatic compound is selected from the group consisting of hydrocarbon aromatics, ring nitrogen-containing aromatics, ring sulfur-containing aromatics and ring oxygen-containing aromatics.

3. The method of claim 1, wherein said iodoaromatic compound is selected from the group consisting of iodobenzenes, iodonaphthalenes, and iodobiphenyls, which are unsubstituted or substituted with one or more one $C_{1-6}$ alkyl group.

4. The method of claim 1, wherein said iodoaromatic compound is selected from the group consisting of iodobenzene, 1-iodonaphthalene, 2-iodonaphthalene, iodobiphenyl and iodotoluene.

5. The method of claim 1, wherein said temperature is about 150°–400° C.

6. The method of claim 4, wherein said temperature is about 175°–350° C.

7. The method of claim 1, wherein said reacting step is conducted in a melt or in solution with an inert solvent.

8. The method of claim 1, wherein said reacting step is conducted with agitation.

9. The method of claim 7, wherein said agitation comprises mechanical stirring or passing air or an inert gas through the reaction mixture.

10. The method of claim 1, wherein said reacting step is conducted as a continuous process.

11. The method of claim 9, wherein an inert gas or air is continuously passed through the reaction mixture in a direction counter to the material flow of the continuous reaction.

* * * * *